(12) United States Patent  
Plumptre

(10) Patent No.: US 9,125,994 B2  
(45) Date of Patent: Sep. 8, 2015

(54) DRUG DELIVERY DEVICE WITH DOSE DIAL SLEEVE ROTATIONAL STOP

(75) Inventor: David Aubrey Plumptre, Worcestershire (GB)

(73) Assignee: SANOFI—AVENTIS DEUTSCHLAND GMBH, Frankfurt am Main (DE)

( * ) Notice: Subject to any disclaimer, the term of this patent is extended or adjusted under 35 U.S.C. 154(b) by 891 days.

(21) Appl. No.: 12/788,767

(22) Filed: May 27, 2010

(65) Prior Publication Data

US 2010/0331791 A1   Dec. 30, 2010

Related U.S. Application Data

(60) Provisional application No. 61/182,853, filed on Jun. 1, 2009.

(30) Foreign Application Priority Data

Jul. 10, 2009   (EP) ..................................... 09009045

(51) Int. Cl.
*A61M 5/31* (2006.01)  
*B23P 17/04* (2006.01)  
*A61M 5/315* (2006.01)  
(Continued)

(52) U.S. Cl.
CPC ............ *A61M 5/31551* (2013.01); *A61M 5/24* (2013.01); *A61M 5/31535* (2013.01); *A61M 5/31548* (2013.01); *A61M 5/31561* (2013.01); *A61M 5/347* (2013.01); *A61M 5/348* (2013.01); *A61M 2005/2407* (2013.01); *A61M 2005/3104* (2013.01); *Y10T 29/49826* (2015.01)

(58) Field of Classification Search
CPC ............ A61M 5/31551; A61M 5/24; A61M 5/31535; A61M 5/31548; A61M 2005/3104; A61M 5/347; A61M 5/348; A61M 2005/2407; A61M 5/31561; A61M 2005/3154; A61M 5/31533
USPC .................................................. 604/207–211
See application file for complete search history.

(56) References Cited

U.S. PATENT DOCUMENTS

| | | | |
|---|---|---|---|
| 3,302,462 | A | 2/1967 | Pursell |
| 5,423,752 | A | 6/1995 | Haber et al. |
| 5,514,097 | A | 5/1996 | Knauer |

(Continued)

FOREIGN PATENT DOCUMENTS

| | | | |
|---|---|---|---|
| DE | 93 01 334 U1 | 4/1993 | |
| DE | 197 30 999 C1 | 12/1998 | |

(Continued)

OTHER PUBLICATIONS

Machine Deisgn, Penton Media, vol. 65, No. 11 (1993) p. 36 "Standard Compression Springs Save Space".

*Primary Examiner* — Theodore Stigell  
(74) *Attorney, Agent, or Firm* — McDonnell Boehnen Hulbert & Berghoff LLP

(57) ABSTRACT

A method and system for a dose setting mechanism of a drug delivery device. The dose setting mechanism includes an inner housing having a helical groove along an external surface of the housing. The inner housing includes a rotational stop feature near one end of the helical groove. The dose setting mechanism also includes a dial sleeve rotatably engaged with the helical groove of the inner housing. When a user rotates the dial sleeve to select a dose, the rotational stop member prevents the user from selecting a dose greater than a pre-defined maximum selectable dose.

14 Claims, 3 Drawing Sheets

(51) Int. Cl.
*A61M 5/24* (2006.01)
*A61M 5/34* (2006.01)

(56) References Cited

U.S. PATENT DOCUMENTS

| | | | |
|---|---|---|---|
| 5,584,815 | A | 12/1996 | Pawelka et al. |
| 5,591,136 | A | 1/1997 | Gabriel |
| 5,792,117 | A | 8/1998 | Brown |
| 5,820,602 | A | 10/1998 | Kovelman et al. |
| 6,090,080 | A | 7/2000 | Jost et al. |
| 6,936,032 | B1 | 8/2005 | Bush, Jr. et al. |
| 8,206,361 | B2 * | 6/2012 | Moller ............ 604/207 |
| 2004/0127858 | A1 | 7/2004 | Bendek et al. |
| 2004/0162528 | A1 | 8/2004 | Horvath et al. |
| 2004/0186437 | A1 | 9/2004 | Frenette et al. |
| 2004/0210199 | A1 | 10/2004 | Atterbury et al. |
| 2004/0236285 | A1 | 11/2004 | Fisher et al. |
| 2005/0137571 | A1 | 6/2005 | Hommann |
| 2006/0153693 | A1 | 7/2006 | Fiechter et al. |
| 2006/0206057 | A1 * | 9/2006 | DeRuntz et al. ............ 604/224 |
| 2006/0258988 | A1 | 11/2006 | Keitel et al. |
| 2007/0021718 | A1 | 1/2007 | Burren et al. |
| 2008/0027397 | A1 | 1/2008 | DeRuntz et al. |
| 2008/0077095 | A1 | 3/2008 | Kirchhofer |
| 2008/0208123 | A1 | 8/2008 | Hommann |
| 2009/0227959 | A1 | 9/2009 | Hirschel et al. |
| 2009/0275915 | A1 * | 11/2009 | Harms et al. .................. 604/506 |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | WO2004/078242 * | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

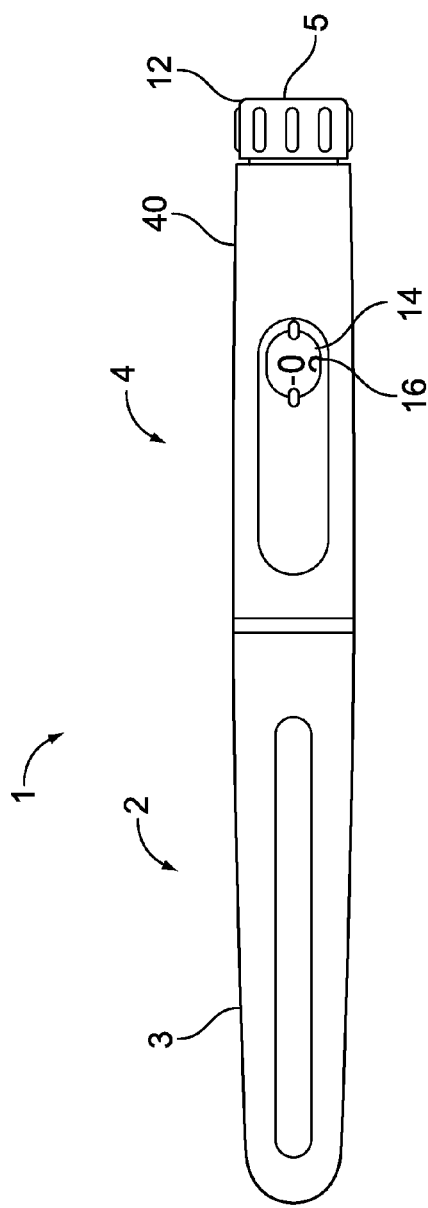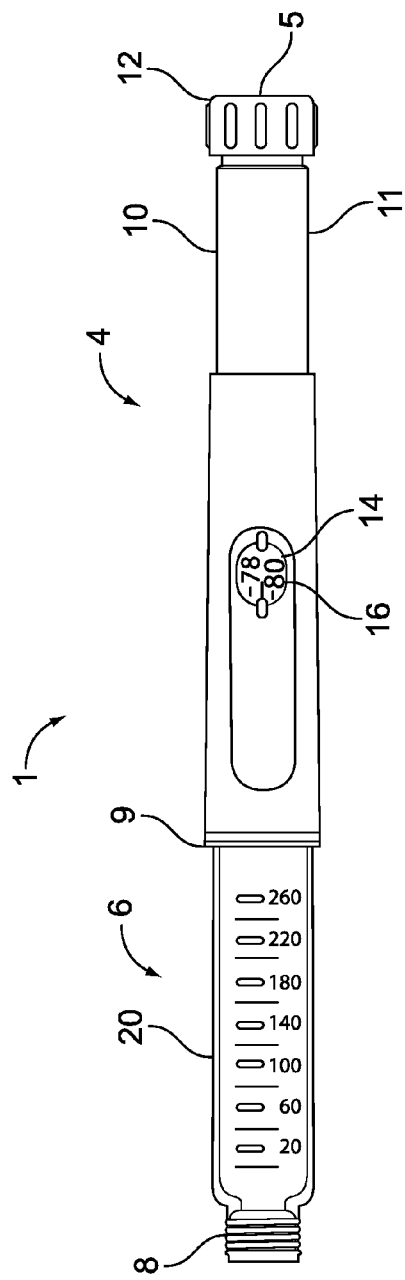
FIG. 1
FIG. 2

DRUG DELIVERY DEVICE WITH DOSE DIAL SLEEVE ROTATIONAL STOP

BACKGROUND

1. Field of the Present Patent Application

The present application is generally directed to dose setting mechanisms for drug delivery devices. More particularly, the present application is generally directed to a dose setting mechanisms comprising an inner housing and a dial sleeve and used for drug delivery devices. Aspects of the invention may be equally applicable in other scenarios as well.

2. Background

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

SUMMARY

According to an exemplary arrangement, a dose setting mechanism for a drug delivery device comprises an inner housing having a helical groove along an external surface of the inner housing and a dial sleeve rotatably engaged with the helical groove of the inner housing. The inner housing comprises a first rotational stop member near one end of the helical groove. When a user rotates the dial sleeve to select a dose, the first rotational stop member prevents the user from selecting a dose greater than a pre-defined maximum selectable dose. The dose dial sleeve may include an inner surface having a helical groove and a second rotational stop member. The first rotational stop member may mate with the second rotational stop member when a user attempts to select a dose greater than the pre-defined maximum selectable dose.

A method of assembling a drug delivery dose setting mechanism is also provided. According to an exemplary arrangement, the method includes establishing a helical groove along an outer surface of an inner housing. The method further includes defining at least one rotational stop feature near one end of the helical groove. The rotational stop feature may reside along the outer surface of the inner housing. The method further includes assembling a dial sleeve over the inner housing by rotating the dial sleeve with respect to the inner housing, where the dial sleeve is in a threaded engagement with the helical groove on the inner housing.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates an embodiment of a drug delivery device;

FIG. 2 illustrates a sectional view of the embodiment of the drug delivery device illustrated in FIG. 1;

DETAILED DESCRIPTION

Figure 3:
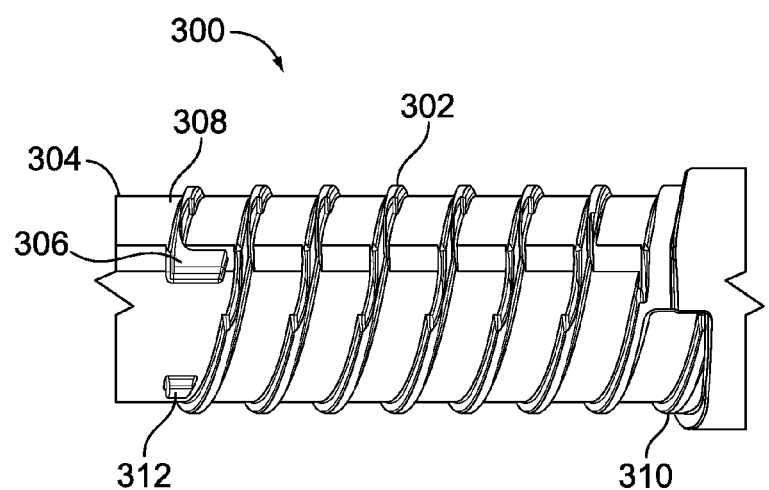
FIG. 3 illustrates a partial view of an embodiment of an inner housing of the drug delivery device illustrated in FIG. 1.

Referring to FIG. 1, there is shown a drug delivery device 1 in accordance with a first arrangement of the present invention. The drug delivery device 1 comprises a housing having a first cartridge retaining part 2, and dose setting mechanism 4. A first end of the cartridge retaining means 2 and a second end of the dose setting mechanism 4 are secured together by retaining features. In this illustrated arrangement, the cartridge retaining means 2 is secured within the second end of the dose setting mechanism 4. A removable cap 3 is releasably retained over a second end or distal end of a cartridge retaining part. As will be described in greater detail, the dose setting mechanism 4 comprises a dose dial grip 12 and a window or lens 14. To set a dose of medication contained within the drug delivery device 1, a user rotates the dose dial grip 12 and the window allows a user to view the dialed dose by way of a dose scale arrangement 16.

FIG. 2 illustrates the medical delivery device 1 of FIG. 1 with the cover 3 removed from the distal end of the medical delivery device. As illustrated, a cartridge 20 from which a number of doses of a medicinal product may be dispensed is provided in the cartridge housing 6. Preferably, the cartridge 20 contains a type of medicament that must be administered often, such as once or more times a day. Once such medicament is insulin. A bung or stopper (not illustrated in FIG. 2) is retained in a first end or a proximal end of the cartridge 20.

The dose setting mechanism 4 of the drug delivery device illustrated in FIG. 2 may be utilized as a reusable (and hence resettable) or a non-reusable (and hence non-resettable) drug delivery device. Where the drug delivery device 1 comprises a reusable drug delivery device, the cartridge is removable from the cartridge housing 6. The cartridge 20 may be removed from the device without destroying the device but merely by the user disconnecting the dose setting mechanism 4 from the cartridge holder 20.

In use, once the removable cap 3 is removed, a user can attach a suitable needle assembly to the distal end of the cartridge holder. Such needle unit may be screwed onto a distal end of the housing or alternatively may be snapped onto this distal end. A replaceable cap 3 is used to cover the cartridge holder 6 extending from the dose setting mechanism 4. Preferably, the outer dimensions of the replaceable cap 3 are similar or identical to the outer dimensions of the dose setting mechanism 4 so as to provide an impression of a unitary whole when the replaceable cap 3 is in position covering the cartridge holder 2.

Returning to FIGS. 1-2, a dose dial grip 12 is disposed about an outer surface of the second end of the dial sleeve 10, which may be a number sleeve. An outer diameter of the dose dial grip 12 preferably corresponds to the outer diameter of the outer housing 40. The dose dial grip 12 is secured to the dial sleeve 10 to prevent relative movement between these two components. In one preferred arrangement, the dose dial grip 12 and number sleeve 10 comprise a one piece component that is rotationally coupled to a clutch and drive sleeve and axially coupled to the number sleeve 10. However, alternative coupling arrangements may also be used.

In normal use, the operation of the dose setting mechanism 4 generally occurs as follows. To dial a dose in the arrangement illustrated in FIGS. 1-2, a user rotates the dose dial grip 12. A user may rotate the dose dial grip towards the user to set a dose. Alternatively, a user may rotate the dose dial grip away from the user to set a dose. A driver, clutch and the dial sleeve 10 rotate along with the dose dial grip 12. The dial sleeve 10 extends in a proximal direction away from the housing 40. In this manner, the driver climbs a spindle. The dial sleeve 10 may extend in a proximal direction away from the housing until a user sets a maximum selectable dose.

FIG. 2 illustrates the medical delivery device after a desired dose of 79 International Units (IU) has been dialed. When this desired dose has been dialed, the user may then dispense the desired dose of 79 IU by depressing the button 5. As the user depresses the button 5, this displaces the clutch axially with respect to the dial sleeve 10, causing the clutch to disengage. However the clutch remains keyed in rotation to the driver. The dial sleeve 10 and associated dose dial grip 12 are now free to rotate. The driver is prevented from rotating with respect to the main housing 40 but it is free to move axially with respect thereto. The longitudinal axial movement of the driver causes the spindle to rotate and thereby to advance a piston in the cartridge 20. The dose setting mechanism in accordance with embodiments prevents a user from selecting a dose greater than a pre-defined maximum selectable dose.

Components of the dose setting mechanism in accordance with embodiments are described in greater detail with reference to FIGS. 3-6.

FIG. 3 illustrates a partial view of an inner housing 300 of the dose setting mechanism 4. As depicted, the inner housing 300 has a helical groove 302 along the external surface 304 of the inner housing. The helical groove 302 is preferably a male helical groove. Alternatively, the helical groove 302 may be a female groove or some other equivalent groove structure.

The inner housing 300 also includes a rotational stop member 306 near one end of the helical groove 302. The helical groove comprises a proximal end 308 and a distal end 310. Preferably, the rotational stop member 306 is located near the proximal end 308 of the helical groove 302. Alternatively, the rotational stop member 306 may be molded on a flexible arm. Molding the rotational stop member 306 on a flexible arm may aid in the assembly of the dose setting mechanism, which is described in more detail below.

Figure 4:
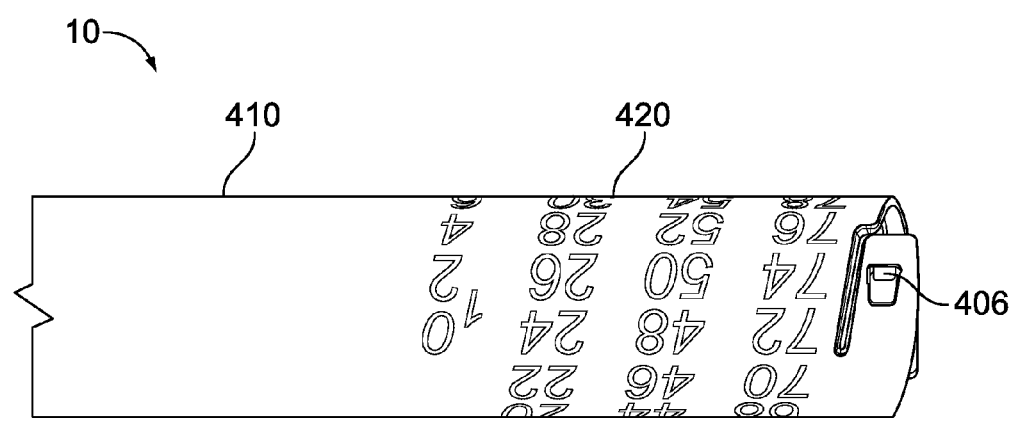
FIG. 4 illustrates an embodiment of a dial sleeve of the drug delivery device illustrated in FIG. 1.
Figure 5:
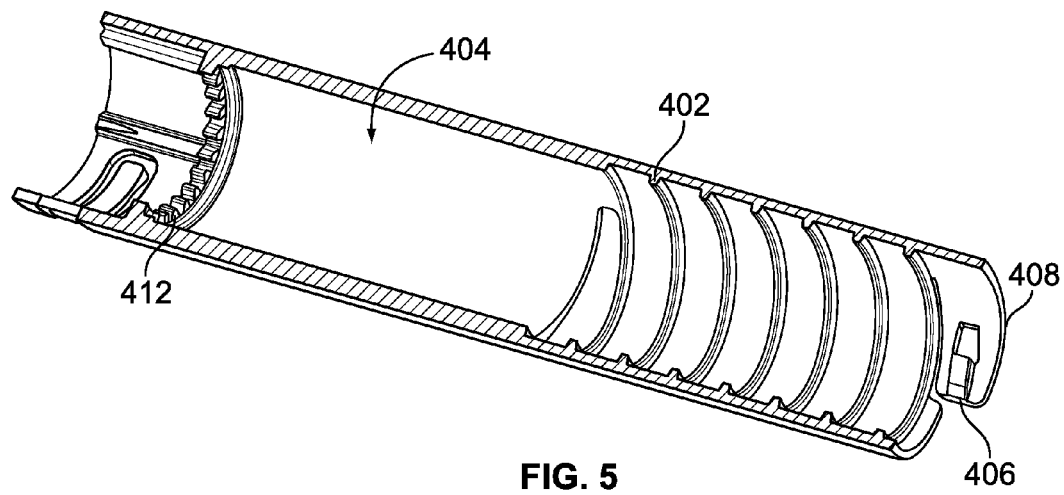
FIG. 5 illustrates a half sectional view of the dial sleeve illustrated in FIG. 4.

FIG. 4 illustrates the dial sleeve 10 of the dose setting mechanism 4. As shown, the dial sleeve 10 is a number sleeve. As is known in the art, the number sleeve may operate to indicate to the user the amount of dose dialed. When the dose setting mechanism is assembled, the dial sleeve 10 is assembled over the inner housing 300. The dial sleeve 10 is capable of rotatably engaging with the helical groove 302 of the inner housing 300. As depicted in FIG. 5, the dial sleeve 10 includes a helical groove 402 on the internal surface 404 of the dial sleeve. The dial sleeve 10 further includes a rotational stop member 406.

In an exemplary arrangement, the inner housing 300 also includes a guide lug 312 on the external surface. Preferably, the guide lug 312 may constrain the helical thread form on the dial sleeve 10. When the dial sleeve 10 is disposed over the inner housing 300, helical groove 402 may engage with the helical groove 302 and the guide lug 312 of the inner housing 300.

When a user of the drug delivery device rotates the dose dial grip of the dose setting mechanism, the first rotational stop member 306 prevents the user from selecting a dose greater than a pre-defined selectable dose, such as a pre-defined maximum selectable dose. Specifically, the first rotational stop member 306 of the inner housing may mate or engage with the second rotational stop member 406 of the dial sleeve 10 when a user attempts to select a dose greater than the pre-defined maximum selectable dose. Rotational stop members 306 and 406 may have complementary undercuts that strengthen the engagement between the two features. The pre-determined maximum selectable dose may be, for example, 80 units. Other pre-defined maximum selectable doses are possible as well.

The rotational stop feature 406 may be on a flexible arm 408. The flexible arm 408 allows the dial sleeve 10 to be easily assembled over the inner housing 300, and this assembly is discussed in greater detail below.

In an exemplary arrangement, the dial sleeve 10 may also comprise clutch features 412 on the internal surface 404. The internal clutch features 412 restrict the design options for de-molding the part. As an example, the clutch features 412 can engage similar features on a drive sleeve so that the number sleeve and drive sleeve rotate together when setting a dose. However, the clutch features 412 disengage when dispensing a dose so as to allow relative rotation. It is advantageous if the groove form 402 on the inner surface 404 of the number sleeve 10 can be molded with an axially moving core pin so as to simplify the mold tool actuation. This can be achieved if the inner groove form 402 comprises less than one turn and the rotational stop feature 406 is molded as a rib extending proximally from one end of the groove form 402 with the an equivalent internal diameter to this groove form. In this manner, the dose dial sleeve 10 can run in the groove between the helical groove 302 on the inner housing. However, the presence of the internal clutch features 412 prevents a core pin from extending proximally out of the part. Consequently, the internal surfaces distal to these clutch features have to be molded with a rotating core pin extending distally from the part.

The dose setting mechanism 4 may also comprise an outer housing 40 that may house the inner housing 300 and the dial sleeve 10 when the dose setting mechanism is assembled. The outer housing 40 preferably has an internal diameter that is equal to or substantially equal to the outer diameter of the dial sleeve 10. Therefore, when the dose setting mechanism is assembled, the outer housing 40 has an internal diameter which defines a clearance fit to the outside diameter of the dial sleeve 10. This clearance fit prevents the flexible rotational stop member 406 on the dial sleeve 10 from disengaging from the rotational stop member 306 on the inner housing when the user attempts to dial beyond the maximum dose stop.

Figure 6:
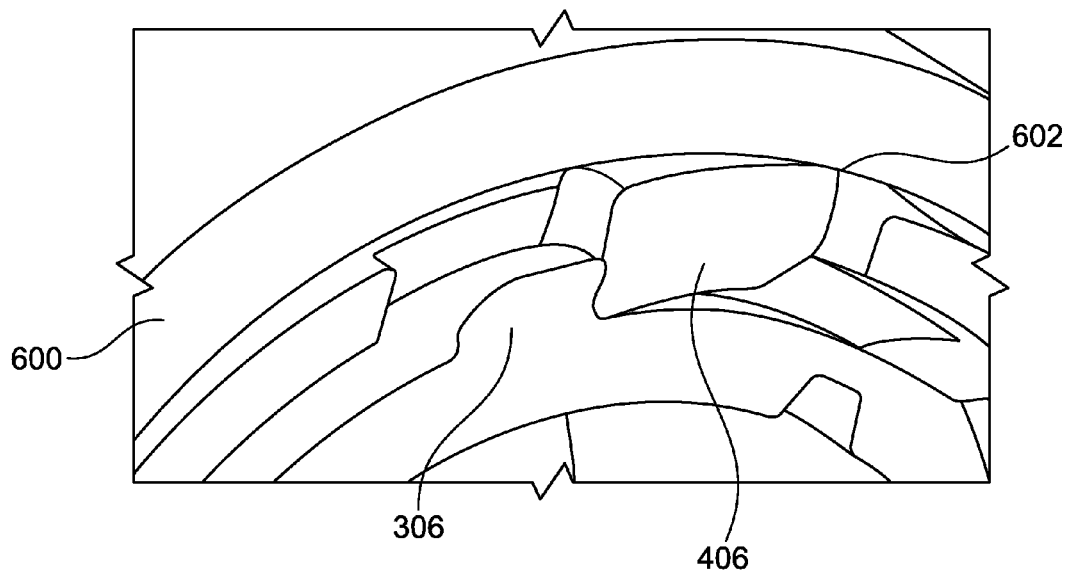
FIG. 6 illustrates the inner housing of FIG. 3 engaged with the dial sleeve of FIGS. 4-5.

FIG. 6 depicts how an exemplary outer housing 600 prevents disengagement of the rotational stop features 306 and 406. As depicted, the rotational stop member 306 engages with the rotational stop member 406 when a user dials the maximum selectable dose. Due to this engagement, the user is prevented from dialing a dose greater than the maximum selectable dose. Under a load, the flexible arm 408 rotates out and contacts the inside surface of the outer housing 600 at point 602, which prevents disengagement from the inner housing stop feature 406. Without the outer housing 600 contacting the rotational stop member 406, the rotational stop member 406 could disengage from rotational stop member 306 under heavy load. The components described in reference to FIGS. 3-6 can be assembled in order to provide a drug delivery dose setting mechanism, such as dose setting mechanism 4. The dial sleeve 10 may be assembled over the inner housing 300 by rotating the dial sleeve 10 with respect to the inner housing 300. As mentioned above, the dial sleeve 10 preferably includes a helical groove 402 that is capable of engaging with the helical groove 302 of the inner housing 300. Further, a rotational stop feature 406 may be provided along the inner surface 404 of the dial sleeve 10, as described above.

During the assembly of the dose setting mechanism, the dial sleeve 10 may be assembled over the inner housing 300, following a helical path during assembly while engaging with the external thread (i.e., the helical groove) on the inner housing. Due to rotational stop member 406 being disposed on the flexible arm 408 and/or rotational stop member 306 being disposed on a flexible arm, the rotational stop features 306 and 406 may pass over one another during assembly. The rotational stop members 306 and 406 may snap over each other during assembly of the dial sleeve over the inner housing. This snapping may occur due to the flexibility of the flexible arm 408 or the flexibility of the rotational stop member 306 (or both) and the absence of the outer housing 600. While the flexible arm or arms allow rotational stops 306 and 406 to pass over one another during assembly, the design of the flexible arms does not allow the rotational stops 306 and 406 to pass over one another when a user dials a dose. Rather, when a user tries to rotate the dial sleeve 10 back out along the helical path 302 by more than the pre-defined maximum selectable dose, the rotational stop members engage one another.

The rotational stop members 306 and 406 may be further prevented from disengagement when the outer housing 600 is assembled over the dial sleeve 10. During the assembly of the dose setting mechanism, the outer housing 600 may be provided over the inner housing 300 and the dial sleeve 10. As mentioned above, the outer housing has an internal diameter, and, when the outer housing 600 is provided over the dial sleeve 10, this internal diameter may be utilized to prevent the rotational stop features of the dose dial sleeve from disengaging the rotational stop features of the inner housing.

In a preferred arrangement, the dose setting mechanism is preferably coupled to a cartridge holder, as depicted in FIGS. 1 and 2. The dose setting mechanism may be permanently coupled to the cartridge holder.

(Advantageously, the inner housing 300 enables the dial sleeve 10 to be provided with a helical groove on an inner surface 404 of the dial sleeve 10, rather than providing such a helical groove on an external surface 410 of the dial sleeve 10. Providing such an internal groove results in a number of advantages. For example, this results in the advantage of providing more surface area along the outer surface 410 of dial sleeve 10 so as to provide the scale arrangement 420. More number dial surface area may be used for drug or device identification purposes.

Having the groove on the inside of the dial sleeve maximizes the area for the dose numbers and minimizes the effective diameter of the groove engagement to the inner housing, thus reducing the risk of this groove interface jamming during dispensing by increasing the effective groove helix angle.

As described, the inner housing 200 also enables the number sleeve 10 to be provided with a helical groove on an inner surface 404 of the number sleeve 10, rather than providing such a helical groove on an external surface of the number sleeve. Providing such an internal groove results in a number of advantages. For example, this results in the advantage of providing more surface area along the outer surface 410 of number sleeve 10 so as to provide the scale arrangement 420. More number sleeve surface area may be used for drug or device identification purposes. Another advantage of providing the helical groove 402 on the inner surface 404 of the drive sleeve is that this inner groove 402 is now protected from dirt ingress. In other words, it is more difficult for dirt to become logged in this inner groove interface than if the groove were provided along the outer surface 410 of the number sleeve 10. This feature is particularly important for a re-settable drug delivery device which will have to function over a much longer period of time compared to a non-resettable device. The effective driving diameter (represented by 'D') of the grooved interface between the number sleeve 10 and the inner housing 200 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the number sleeve will rotate or lock to the inner body wherein this helix angle is proportional to the ratio of P/D. Because the dial sleeve 10 has the helical groove 402 on the internal surface 404 of the dial sleeve, the outer surface 410 may be a generally smooth outer surface.

By utilizing the inner housing 300 and the dial sleeve 10, the dose setting mechanism 4 results in certain manufacturing advantages as well. For example, in one preferred arrangement, the dial sleeve 10 may be molded as a single component. The design of the dial sleeve 10 in accordance with embodiments allows the dial sleeve to be molded as a single component. Molding the dial sleeve as a single component may beneficially lower manufacturing and/or assembly costs.

Another advantage of a dose setting mechanism in accordance with this arrangement is that the dose setting mechanism 4 has a reduced number of components over other known dose setting mechanisms In other words, the dial sleeve 10 is a single component having the clutch features 412, the inner groove mating with the outer groove on the inner housing and the maximum dose stop features acting between these two parts.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for a drug delivery device, said mechanism comprising:
   an outer housing;

an inner housing having a helical groove along an external surface of said inner housing, said inner housing comprising a first rotational stop member near one end of said helical groove, wherein the first rotational stop member comprises a first flexible arm member; and a dial sleeve having internal and external surfaces where the internal surface is rotatably engaged with said helical groove of said inner housing and where the external surface does not contain a helical groove and comprises a generally smooth outer surface, wherein, when a user rotates said dial sleeve to select a dose, said first rotational stop member prevents said user from selecting a dose greater than a pre-defined maximum selectable dose, wherein the internal surface of the said dial sleeve comprises an inner surface having a helical groove and a second rotational stop member, wherein said first rotational stop member of said inner housing engages with said second rotational stop member of said dial sleeve when a user attempts to select a dose greater than said pre-defined maximum selectable dose, wherein said second rotational stop member comprises a second flexible arm member, and wherein the second flexible arm member rotates out and contacts an internal surface of the outer housing when a user attempts to select a dose greater than said pre-defined maximum selectable dose.

2. The invention of claim 1 wherein said one end of said helical groove of the inner housing comprises a proximal end of said helical groove.

3. The invention of claim 1 wherein said dial sleeve is a single molded component.

4. The invention of claim 1 wherein said helical groove of said inner housing comprises a male helical groove.

5. The invention of claim 1 wherein the helical groove of the dial sleeve comprises a male helical groove that rotatably engages said helical groove of said inner housing.

6. The invention of claim 1 wherein said dose setting mechanism is coupled to a cartridge holder.

7. The invention of claim 6 wherein said dose setting mechanism is permanently coupled to said cartridge holder.

8. The invention of claim 7 wherein said cartridge holder comprises a removable cartridge.

9. The invention of claim 1 wherein said dial sleeve is rotated towards a user to set a dose.

10. A method of assembling a dose setting mechanism according to claim 1, said method comprising the steps of:

establishing the helical groove along the external surface of the inner housing; defining the first rotational stop member near one end of said helical groove, said first rotational stop member residing along said external surface of said inner housing and comprises the first flexible arm member; and assembling the dial sleeve over said inner housing by rotating said dial sleeve with respect to said inner housing, said dial sleeve in threaded engagement with said helical groove.

11. The method of claim 10 further comprising the step of snapping said at second rotational stop feature of said dial sleeve over said first rotational stop feature of said dial sleeve when said dial sleeve is assembled over said inner housing.

12. The method of claim 10 further comprising the step of providing an outer housing having an internal diameter over said dial sleeve, and utilizing said internal diameter of said outer housing to prevent said rotational stop features of said dial sleeve from disengaging from said rotational stop features of said inner housing.

13. The method of claim 10 further comprising coupling said dose setting mechanism to a cartridge holder.

14. The method of claim 10 further comprising the step of molding said dial sleeve as a single component.

* * * * *